(12) United States Patent
Stinson

(10) Patent No.: US 8,137,614 B2
(45) Date of Patent: Mar. 20, 2012

(54) MEDICAL DEVICES AND METHOD FOR MAKING THE SAME

(75) Inventor: Jonathan S. Stinson, Minneapolis, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 12/643,629

(22) Filed: Dec. 21, 2009

(65) Prior Publication Data

US 2010/0228334 A1 Sep. 9, 2010

Related U.S. Application Data

(63) Continuation of application No. 10/672,891, filed on Sep. 26, 2003, now abandoned.

(51) Int. Cl.
*C22C 14/00* (2006.01)
*A61F 2/06* (2006.01)

(52) U.S. Cl. ........................ 420/417; 623/1.15

(58) Field of Classification Search ................ 623/1.15; 420/417
See application file for complete search history.

(56) References Cited

U.S. PATENT DOCUMENTS

| | | | | |
|---|---|---|---|---|
| 3,161,503 A * | 12/1964 | Lenning et al. | | 420/580 |
| 3,549,429 A * | 12/1970 | Rausch et al. | | 428/610 |
| 4,040,129 A | 8/1977 | Steinemann et al. | | |
| 4,994,071 A * | 2/1991 | MacGregor | | 606/194 |
| 5,169,597 A | 12/1992 | Davidson et al. | | |
| 5,195,969 A | 3/1993 | Wang et al. | | |
| 5,232,361 A * | 8/1993 | Sachdeva et al. | | 433/8 |
| 5,270,086 A | 12/1993 | Hamlin | | |
| 5,366,504 A | 11/1994 | Andersen et al. | | |
| 5,383,928 A * | 1/1995 | Scott et al. | | 623/1.12 |
| 5,545,227 A | 8/1996 | Davidson et al. | | |
| 5,643,312 A * | 7/1997 | Fischell et al. | | 623/1.15 |
| 5,690,670 A | 11/1997 | Davidson | | |
| 5,728,158 A * | 3/1998 | Lau et al. | | 623/23.7 |
| 5,780,807 A | 7/1998 | Saunders | | |
| 5,843,168 A * | 12/1998 | Dang | | 623/1.15 |
| 5,888,201 A | 3/1999 | Stinson et al. | | |
| 5,954,724 A | 9/1999 | Davidson | | |
| 5,972,027 A | 10/1999 | Johnson | | |
| 6,027,528 A | 2/2000 | Tomonto et al. | | |
| 6,146,404 A | 11/2000 | Kim et al. | | |
| 6,171,327 B1 | 1/2001 | Daniel et al. | | |
| 6,200,685 B1 | 3/2001 | Davidson | | |
| 6,258,182 B1 | 7/2001 | Schetky et al. | | |
| 6,280,457 B1 | 8/2001 | Wallace et al. | | |
| 6,342,062 B1 | 1/2002 | Suon et al. | | |

(Continued)

FOREIGN PATENT DOCUMENTS

EP 0 359 446 3/1990

(Continued)

OTHER PUBLICATIONS

ASM International, Material Park, Ohio, Properties and Selection-:Nonferrous Alloys and Special-Purpose Materials, "Introduction to Titanium and Titanium Alloys", Oct. 1990, vol. 2, pp. 586-591.*

(Continued)

*Primary Examiner* — Jessee R. Roe
(74) *Attorney, Agent, or Firm* — Fish & Richardson P.C.

(57) ABSTRACT

Medical devices, such as stents, and methods of the devices are described.

8 Claims, 8 Drawing Sheets

U.S. PATENT DOCUMENTS

| | | | |
|---|---|---|---|
| 6,375,458 | B1 | 4/2002 | Moorleghem et al. |
| 6,409,852 | B1 | 6/2002 | Lin et al. |
| 6,468,266 | B1 | 10/2002 | Bashiri et al. |
| 6,676,987 | B2 | 1/2004 | Zhong et al. |
| 6,767,418 | B1 | 7/2004 | Zhang et al. |
| 7,462,366 | B2 | 12/2008 | Lanphere et al. |
| 2004/0143317 | A1 | 7/2004 | Stinson et al. |

FOREIGN PATENT DOCUMENTS

| | | |
|---|---|---|
| EP | 0 947 204 | 10/1999 |
| WO | 00/61203 | 10/2000 |
| WO | 02/78764 | 10/2002 |

OTHER PUBLICATIONS

Laissy et al., "Magnetic Resonance Angiography of Intravascular Endoprostheses: Investigation of Three Devices," *Cardiovasc Intervent Radiol*, 1995, 18:360-366.

Ortiz et al., "Thermomechanical Analysis of Ti40Ta and Ti50Ta Alloys," *Structural Biomaterials for the 21st Century*, 2001, pp. 35-42.

Schenck, "The role of magnetic susceptibility in magnetic resonance imaging: MRI magnetic compatiblity of the first and second kinds," *Med. Phys.*, 1996, 23(6):815-850.

Shellock et al., "MR Imaging and Biomedical Implants, Materials, and Devices: An Updated Review," *Radiology*, 1991, 180:541-550.

Taal et al., "Potential risks and artifacts of magnetic resonance imaging of self-expandable esophageal stents," *Gastrointestinal Endoscopy*, 1997, 46(5):424-429.

U.S. FDA, "A Primer on Medical Device Interactions with Magnetic Resonance Imaging Systems," http://www.fda.gov/cdrh/ode/primerf6.html, 17 pages, released Feb. 7, 1997.

Zardiackas et al., "Characterization of Ti-15Mo Beta Titanium Alloy," 1997, pp. 95-98.

"Standard Test Method for Evaluation of MR Image Artifacts from Passive Implants," *ASTM* Designation:F2119-01, 2001, pp. 1-3.

List of references, "ti-ta alloys lit search.txt", 27 pages.

List of references, "Jan. 2002 Nerac literature search for Ti-Ta and Ti-Mo alloys", retrieved in Jan. 2002 from Nerac, 12 pages.

*Coronary Stenting—Current Perspectives—A Companion to the Handbook of Coronary Stents*, Michael JB Kutryk & Patrick Serruys, pp. 1-16 (Copyright 1999).

Partial International Search Report in PCT/US2004/030645 mailed Feb. 18, 2005.

* cited by examiner

MEDICAL DEVICES AND METHOD FOR MAKING THE SAME

CLAIM OF PRIORITY

This application claims priority under 35 USC §119(e) to U.S. patent application Ser. No. 10/672,891, filed on Sep. 26, 2003 now abandoned, the entire contents of which are hereby incorporated by reference.

TECHNICAL FIELD

The invention relates to medical devices, such as, for example, stents and stent-grafts, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents and covered stents, sometimes called "stent-grafts".

An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

When the endoprosthesis is advanced through the body, its progress can be monitored, e.g., tracked, so that the endoprosthesis can be delivered properly to a target site. After the endoprosthesis is delivered to the target site, the endoprosthesis can be monitored to determine whether it has been placed properly and/or is functioning properly.

Monitoring of the position of the endoprosthesis during implantation is typically performed by a radiographic technique such as fluoroscopy. The radiographic density of the metal endoprosthesis is different from bone and tissue, and the device is observed in the fluoroscopic image from the visible difference in contrast and grey scale relative to the surrounding biological material. The disadvantage of fluoroscopy is that the physician, staff, and patient are exposed to ionizing radiation which can be harmful in strong or repeated doses.

Another method of monitoring a medical device is magnetic resonance imaging (MRI). MRI uses a magnetic field and radio waves to image the body. In some MRI procedures, the patient is exposed to a magnetic field, which interacts with certain atoms, e.g., hydrogen atoms, in the patient's body. Incident radio waves are then directed at the patient. The incident radio waves interact with atoms in the patient's body, and produce characteristic return radio waves. The return radio waves are detected by a scanner and processed by a computer to generate an image of the body.

SUMMARY

In an aspect, the invention features a balloon-expandable medical stent. The stent includes a generally tubular body including an alloy having Ti at about 20 weight percent or more and at least one of Zr, Ta, or Mo. The alloy has a yield strength of about 45 ksi or more, a magnetic susceptibility of about +1 or less, and a mass absorption coefficient of about 1.9 $cm^2/g$ or more.

In another aspect, the invention features a system including a catheter for delivery into a body lumen. The catheter includes an expandable member and a stent as described herein disposable over the expandable member. The expandable member is expandable to a maximum diameter of about 1.55 mm to about 14 mm.

In another aspect, the invention features an implantable medical device including an alloy having Ti at about 20 weight percent or more and at least one of Zr, Ta, or Mo, a yield strength of about 45 ksi or more, a magnetic susceptibility of about +1 or less, and a mass absorption coefficient of about 1.9 $cm^2/g$ or more. The medical device can be a filter, a guidewire, a catheter, a needle, a biopsy needle, a staple, or a cannula.

In another aspect, the invention features a method of forming a stent. The method includes providing an alloy including Ti of about 20 weight percent or more and at least one of an additive selected from Zr, Ta or Mo. The method includes contacting solid aliquots of a titanium component selected from Ti or a Ti-containing alloy, and the additive heating the aliquot after the contacting, and mechanically working the aliquots after contacting by forging, extrusion, drawing or rolling, melting the aliquots, forming an ingot, forming a tube including the alloy, and incorporating the tube into a stent.

In an aspect, the invention features a method of forming a medical device. The method includes providing a metal alloy of multiple components of elements or alloys, including a first component and a second component having a melting point difference of about 150° C. or more. Solid aliquots of the first component and the second component are contacted, heated and/or mechanically worked, then the worked components are melted. The alloy is incorporated into a medical device.

In another aspect, the invention features a medical device including an alloy that exhibits one or more (e.g., two, three, or four) properties selected from radiopacity, MRI capability, mechanical properties, and/or biocompatibility properties as described herein, in any combination. In other aspects, the invention features particular alloys and techniques for making the alloys.

In yet another aspect, the invention features a medical device including a titanium alloy having at least one of zirconium, tantalum, molybdenum, or niobium. The alloy exhibits radiopacity, MRI capability, mechanical properties, and/or biocompatibility properties, and combinations of the properties as described herein. In other aspects, the invention features particular alloys and techniques for making the alloys.

Embodiments may include one or more of the following advantages. A stent or other medical device is provided that includes desirable magnetic imaging radiopacity, biocompatibility and/or mechanical characteristics. For example, the stent is less susceptible to magnetic resonance image degradation (e.g., less than stainless steel) Implant movement or heating can be reduced. The stent alloy has sufficient radiopacity that the stent is visible by fluoroscopy. The mechanical characteristics of the alloy enable a stent of conventional design that can be delivered into the body in a reduced diameter configuration and then expanded at a treatment site, e.g., by a balloon catheter. The titanium alloys generally can exhibit enhanced strength, stiffness and radiopacity, while maintaining low magnetic susceptibility.

Still further aspects, features, and advantages follow.

DETAILED DESCRIPTION

Structure and Alloy Formulation

Figure 1A:
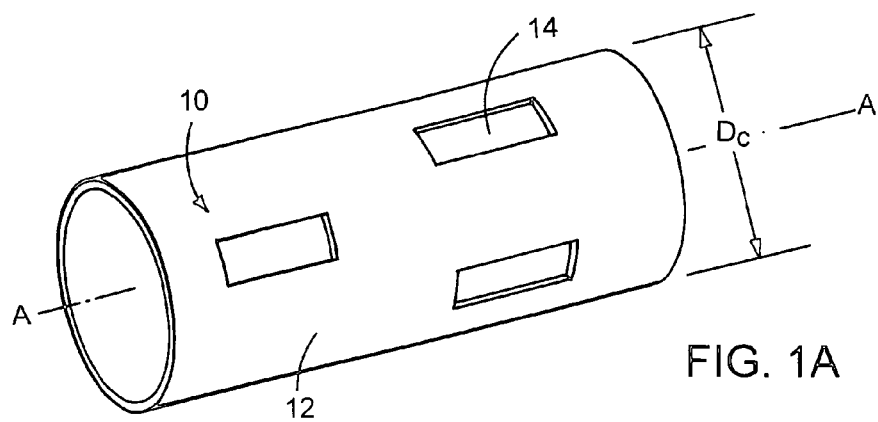
FIGS. 1A and 1B are perspective views of a stent in a compressed and expanded condition, respectively.
Figure 1B:
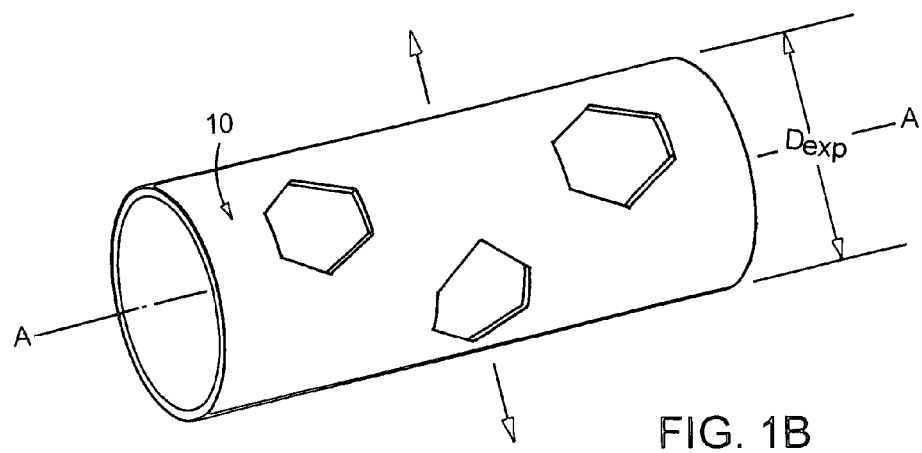

Referring to FIGS. 1A and 1B, a stent 10 includes a metal body 12 in the shape of a tube. The metal body includes aperture regions 14 provided in a pattern to facilitate stent functions, such as radial expansion, and lateral flexibility. Between aperture regions are strut regions 16. Referring particularly to FIG. 1A, for delivery into the body, the stent 10 is provided or maintained in a relatively small diameter condition corresponding to a diameter D. Referring to FIG. 1B, upon placement at the treatment site, the stent 10 is expanded to a larger diameter, $D_{exp}$, so that the stent is in contact with the lumen wall. The stent may be expanded by a mechanical expander, such as an inflatable balloon, or it may be self-expanding. The metal body of the stent may be formed by a generally continuous sheet or by filaments that are wrapped, braided, knitted or otherwise configured to generally define a stent.

Figure 2A:
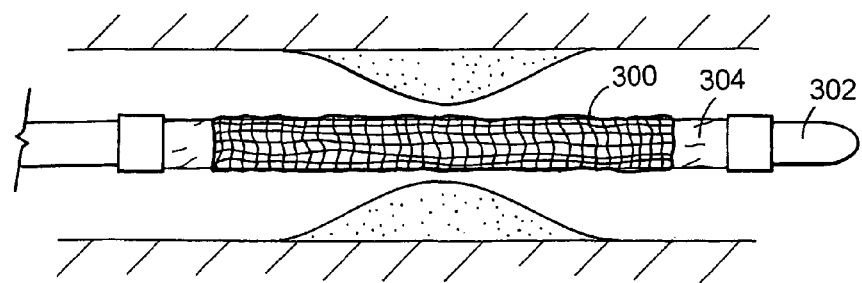
FIGS. 2A-2C illustrate delivery of a balloon expandable stent.
Figure 2B:
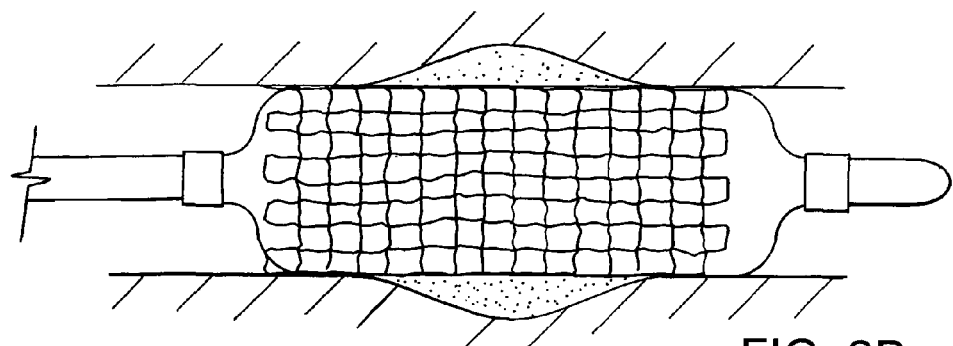
Figure 2C:
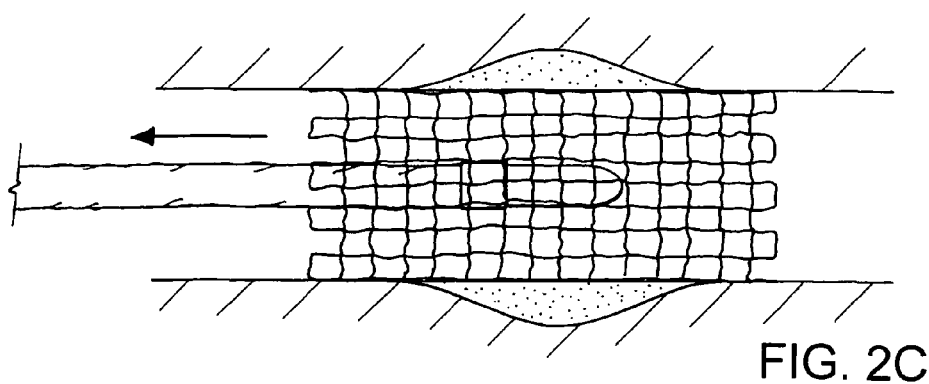

Referring now to FIGS. 2A-2C, the delivery of a balloon-expandable stent is illustrated. The stent 300 is carried on a catheter 302 over a balloon 304. When the treatment site is reached, the balloon is expanded to expand the stent into contact with the lumen wall. The stent may be used in the vascular system (e.g., in the coronary or peripheral arteries), or in other body lumens.

The stent body is formed of a metal alloy that has desirable magnetic resonance, radiopacity, biocompatibility, and/or mechanical characteristics. In embodiments, the alloy is a titanium-containing alloy that includes one or more of Zr, Ta or Mo. In particular embodiments, the alloy is formed from commercially pure (CP) titanium or Ti-6Al-4V ELI, which has been alloyed with one or more of Zr, Ta, or Mo by processes that include mechanical or diffusion alloying followed by melting, as will be described below.

The alloy is formulated to provide desired characteristics. For MRI compatibility, the alloy is formulated to reduce signal distortion, electrical current (e.g., eddy current) generation, heating, movement within the body or nerve simulation, by controlling the magnetic susceptibility and solubility of the alloy constituents. The magnetic susceptibilities of Ti, Zr, Ta, and Mo and other materials are provided in Table I.

TABLE I

| Magnetic Susceptibilities | |
|---|---|
| Material: | Magnetic Susceptibility: |
| Water at 37° C. | $-9.05 \times 10^{-6}$ |
| Human tissues | $-11.0 \times 10^{-6}$ to $-7.0 \times 10^{-6}$ |

TABLE I-continued

| Magnetic Susceptibilities | |
|---|---|
| Material: | Magnetic Susceptibility: |
| copper | $-9.63 \times 10^{-6}$ |
| ferromagnetic iron | $+10^5$ |
| magnetic stainless steel (martensitic) | $+10^3$ |
| stainless steel (austenitic) | $+3.5 \times 10^{-3}$ to $+6.7 \times 10^{-3}$ |
| heavily cold worked stainless steel (austenitic) | $+1$ to $+10$ |
| Nitinol (Ni—Ti) | $+0.245 \times 10^{-3}$ |
| zirconium | $+0.109 \times 10^{-3}$ |
| titanium | $+0.182 \times 10^{-3}$ |
| niobium | $+0.237 \times 10^{-3}$ |
| platinum | $+0.279 \times 10^{-3}$ |
| molybdenum | $+0.123 \times 10^{-3}$ |
| tantalum | $+0.178 \times 10^{-3}$ |

In embodiments, the magnetic susceptibility of the alloy is less than the magnetic susceptibility of austenitic stainless steel, e.g. about +1 or less or about $3.5 \times 10^{-3}$ or less. Solubility of the constituents can be determined by binary phase diagrams. Suitable solubility is indicated by a single phase (alpha or beta) or by a two phase solution (alpha and beta) at room temperature. Examples of suitable phase diagrams are available in the ASM Handbook, volume 3, ASM International, 1992, the entire contents of which is hereby incorporated by reference.

For radiopacity, the alloy is formulated to a desired mass absorption coefficient. Preferably, the stent is readily visible by fluoroscopy, but does not appear so bright that detail in the fluoroscopic image is distorted. In some embodiments, the alloy or the device has a radiopacity of from about 1.10 to about 3.50 times (e.g., greater than or equal to about 1.1, 1.5, 2.0, 2.5, or 3.0 times; and/or less than or equal to about 3.5, 3.0, 2.5, 2.0, or 1.5 times) that of 316L grade stainless steel, as measured by ASTM F640 (Standard Test Methods for Radiopacity of Plastics for Medical Use). Mass absorption coefficients and densities or Ti, Ta, Zr and Mo are compared to 316L stainless steel in Table II.

TABLE II

| Mass Absorption Coefficients | | | | | |
|---|---|---|---|---|---|
| | | Alloy | | | |
| | 316L SS | Ti | Ta | Zr | Mo |
| Mass absorption coefficient, $cm^2/g$ | 1.96 (Fe) | 1.21 | 5.72 | 6.17 | 7.04 |
| Density, g/cc | 8.0 | 4.5 | 16.7 | 6.5 | 10.2 |

In embodiments, the mass absorption coefficient of the alloy is about 1.96 $cm^2/g$ (corresponding substantially to the mass absorption coefficient of Fe) to about 2.61 $cm^2/g$ (corresponding to about 0.5 the mass absorption coefficient of Ta). Mass absorption coefficient can be calculated from the results of radiopacity tests, as described in *The Physics of Radiology*, H. E. Johns, J. R. Cunningham, Charles C. Thomas Publisher, 1983, Springfield, Ill., pp. 133-143. A calculation of alloy mass absorption coefficient is provided in the examples, infra.

For desirable mechanical properties, the alloy is formulated based on solubility and phase structure. In particular embodiments, the alloy exhibits certain mechanical properties within about ±20% (e.g., within about ±10%, about ±5%, or about ±1%) of the corresponding value for stainless steel. Mechanical properties for select materials are provided in Table III.

TABLE III

Mean Tensile Test Data (Annealed Condition)

| Tubing | 0.2% offset Ys, ksi | % strain to peak load | UTS, ksi | % strain to fracture | E, msi |
|---|---|---|---|---|---|
| 316L SS | 50 | 36 | 94 | 45 | 29 |
| Tantalum | 24 | No data | 35-70 | 40 | 27 |
| CP Titanium | 25-70 | No data | 35-80 | 15-25 | 15 |
| Ti—6Al—4V ELI | 120 | No data | 130 | 15 | 17 |

Yield strength (YS) relates to the applied pressure needed to flow the alloy to expand the stent. The percent strain to peak load indicates how far the material can strain before necking occurs. The ultimate tensile strength (UTS) is the stress value that corresponds with strain to peak load. The percent strain to fracture is a measure of how far the material can be stretched prior to break, and includes uniform deformation plus location deformation in the necked down region. This property relates to stent strut fracture from over-expansion of the stent. Suitable test methods for determining these parameters are described in ASTM E8 (Standard Test Methods for Tension Testing of Metallic Materials). In Table III, the 316L SS properties were measured from annealed stent tubing. The other material properties were taken from handbooks, such as *American Society for Metals Handbook Desk Edition*, H. E. Boyer, T. L. Gall, 1985.

The solubility of the constituents and phase structure of the alloy is indicated by phase diagrams. Suitable solubilities are indicated by alpha and/or beta microstructures without substantial amounts of more brittle phases such as alpha prime, alpha double prime or omega phases. Active rapid cooling after melting can be utilized to reduce precipitation of these phases. In embodiments, the presence of brittle phases is less than about 10% (e.g., less than about 7%, 5%, or 3%) as measured by X-ray diffraction analysis. The presence of two phases is preferably equal to or less than the amount in commercially available Ti-6Al-4V (available from Allegheny Technologies Allvac (Monroe, N.C.) or Metalmen Sales (Long Island City, N.Y.). Alloying Ti with Ta and Mo increases modulus of elasticity. Alloying Ti with Ta, Mo, and/or Zr increases tensile strength. In embodiments, tensile properties are balanced by annealing the alloy. For example, annealing time and temperature can be selected to produce a maximum level of ductility while meeting minimum design requirements for yield strength and grain size. Alternatively or in addition, the stent design can be modified to accommodate less favorable mechanical properties. For example, for a lower tensile elongation (% strain to fracture) the stent is designed to lower the strain on the struts during expansion, such as by increasing the number of deformation "hinge" points in the stent so that the total stent deformation is distributed in smaller amounts to the areas where deformation occurs.

Biocompatibility of the stent is provided by alloying biocompatible constituents or coating the sent with a biocompatible material. Biocompatibility can be tested by using industry standard ISO 10992 in-vitro and in vivo test methods, which can provide a qualitative pass or fail indication. In embodiments, the stent has a biocompatibility similar to or equivalent to pure titanium or pure tantalum, as measured by ISO 10992 test methods.

In embodiments, the alloy constituents are provided in combinations and amounts recited in the Summary and Examples. In particular embodiments, the alloy is Ti—Ta, Ti—Mo, Ti—Zr, Ti—Ta—Mo, Ti—Ta—Zr, Ti—Ta—Zr—Mo, Ti—Zr—Mo or Ti 6Al-4V—Ta, Ti 6Al-4V—Mo, Ti 6Al-4V—Zr, Ti 6Al-4V—Ta—Mo, Ti 6Al-4V—Ta—Zr, Ti 6Al-4V—Ta—Zr—Mo, or Ti 6Al-4V—Zr—Mo alloy. In other embodiments, Ti-13Nb-13Zr, Ti-8Al-1Mo-1V, Ti-6Al-2Nb-1 Ta-0.8Mo and Ti-7Al-4Mo one alloyed with Ta, Mo, and/or Zr. In particular embodiments, the alloy is annealed. In particular embodiments, the alloy is formed by alloying CP titanium or Ti-6Al-4V ELI with Ta, Zr and/or Mo. In embodiments, the alloy includes 40 to 70 weight percent tantalum or 25 to 50 weight percent zirconium with CP titanium or Ti-6Al-4V ELI. In embodiments, 5 to 20 weight percent molybdenum is added in place of some of the titanium for added tensile strength without sacrificing MRI compatibility. Suitable alloys include the following:

| CP Titanium alloyed with: | Ti—6Al—4V ELI alloyed with: |
|---|---|
| 43 weight % Ta | 43 weight % Ta |
| 69 weight % Ta | 69 weight % Ta |
| 25 weight % Ta | 25 weight % Ta |
| 49 weight % Zr | 49 weight % Zr |
| 43 weight % Ta + 5% Mo | 43 weight % Ta + 5% Mo |
| 69 weight % Ta + 5% Mo | 69 weight % Ta + 5% Mo |
| 25 weight % Zr + 5% Mo | 25 weight % Zr + 5% Mo |
| 49 weight % Zr + 5% Mo | 49 weight % Zr + 5% Mo |
| 43 weight % Ta + 10% Mo | 43 weight % Ta + 10% Mo |
| 69 weight % Ta + 10% Mo | 69 weight % Ta + 10% Mo |
| 25 weight % Zr + 10% Mo | 25 weight % Zr + 10% Mo |
| 49 weight % Zr + 10% Mo | 49 weight % Zr + 10% Mo |
| 22 weight % Ta + 13% Zr | 22 weight % Ta + 13% Zr |
| 35 weight % Ta + 25% Zr | 35 weight % Ta + 25% Zr |

Manufacture

Figure 3:
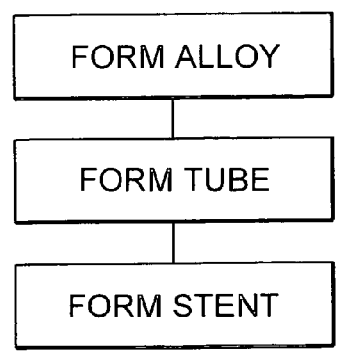
FIG. 3 is a flow diagram of a stent manufacturing process.

Referring to FIG. 3, a stent is constructed by forming an alloy, forming a tube from the alloy, and then forming the tube into a stent.

Referring to FIGS. 4A to 4E, an alloying process is illustrated for forming an ingot or billet of a size and form suitable for stent construction.

Figure 4A:
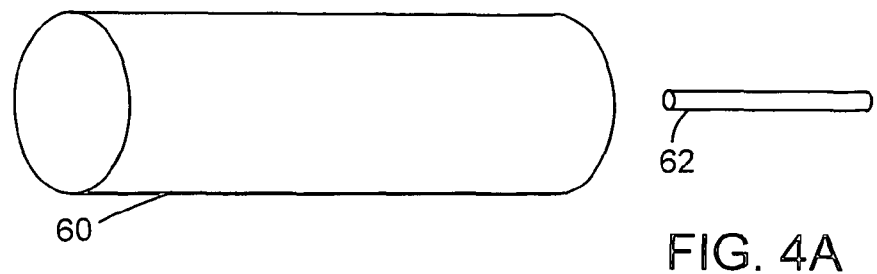
FIGS. 4A-4F illustrate a process for making a medical device.

Referring to FIG. 4A, a base rod 60 and one or more additive rods 62 are provided. For example, the base rod is Ti or a Ti-containing alloy and the additive rod(s) are Ti, Ta, Zr, and/or Mo. The weight of the rods are in proportion to the desired alloy formulation.

Figure 4B:
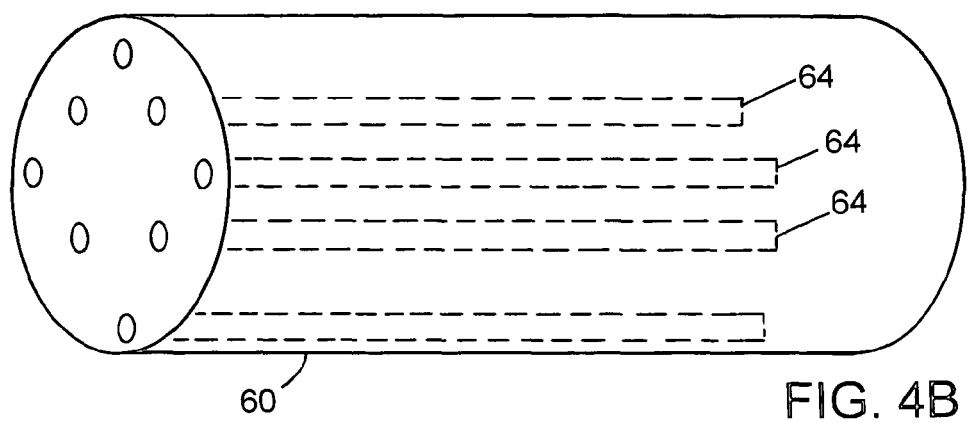

Referring to FIG. 4B, the base rod is drilled to provide voids 64.

Figure 4C:
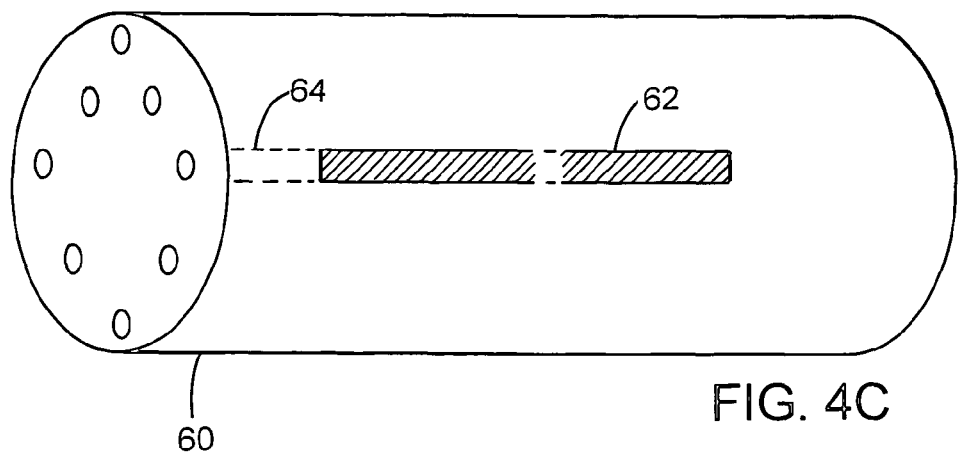

Referring to FIG. 4C, additive rods 62 are inserted into the voids 64 of the base rod 60.

Figure 4D:
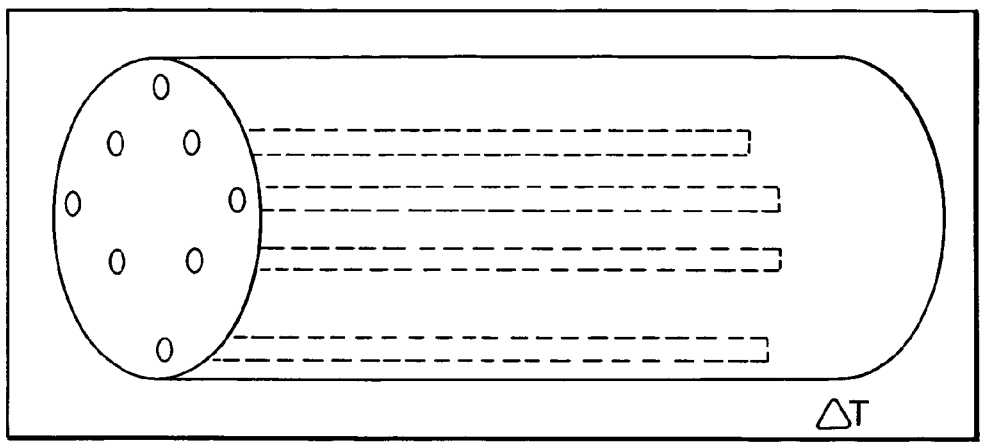

Referring to FIG. 4D, this assembly is prealloyed by heating and/or mechanically working to cause diffusion alloying between constituents.

Figure 4E:
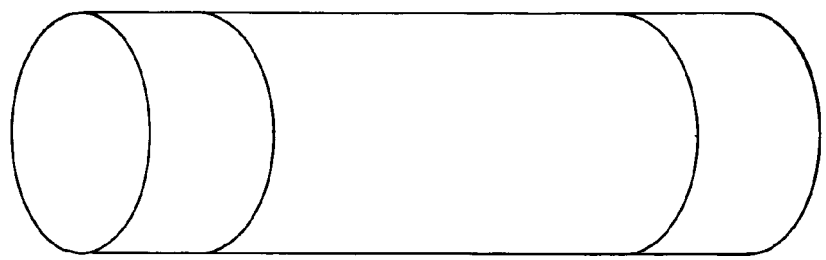

Referring to FIG. 4E, the assembly is provided with end caps to prevent additive rods 62 from falling out of base rod 60. The assembly is melted and cast once or multiple times in a vacuum are remelt (VAR) furnace, EB melting furnace, VIM furnace, or levitation melting furnace to allow liquid-phase alloying to occur.

Figure 4F:
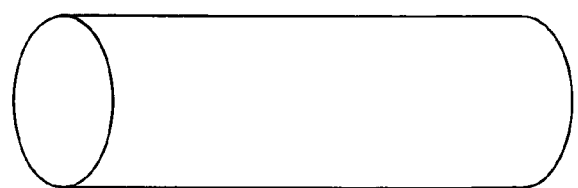

Referring to FIG. 4F, the alloy (e.g., the alloyed billet is suitable for further processing. The billet can be drawn into tubing or rolled into a sheet for stock stent tubing production. For example an ingot or billet 2.5 inches in diameter by 4 inches long can typically yield at least 1000 feet of coronary stent tubing.

The alloying process is particularly advantageous for alloying constituents with large melting temperature differences. In Table IV, the melting temperatures of Ti, Ta, Zr, and Mo are provided.

TABLE IV

Melting Temperatures

| Element | Melting Temperature, ° C. |
|---|---|
| Ti | 1668 |
| Ta | 2996 |
| Zr | 1852 |
| Mo | 2610 |

The melting temperature difference between Ti and Zr, and Ta and Mo is over 500° C. The difference between Ti and Zr is over 150° C. In the method of FIG. 4A et seq., aliquots of constituents of the alloy are intimately contacted, mechanically and/or diffusion alloyed and then melted and cast into ingot. By diffusion or mechanical alloying the aliquots, less overall mixing is required in the melting and casting furnace.

In the prealloying step, heating is performed in an inert gas or vacuum, or the outer surfaces of the billet could be coated or canned with a protective metal, such as iron, that could later be chemically dissolved. After drilling and filling or after the diffusion heat treatment, the billet can also be extruded, drawn, or rolled to further consolidate the assembly. The heat treatment or working serves to hold additive material in place within the billet during melting. Also, constituents with high melting points can be essentially encapsulated within, e.g. titanium, minimizing the exposure to any residual air in the casting furnace. For diffusion heating, the assembly can be heated near the melting temperature of the lowest melting temperature constituent and/or the melting temperature of the material of the base rod. For example, for a Ti base rod, the temperature is about 1600° C. or less.

In embodiments, additives to the base are made in incremental steps in each of multiple melting and ingot casting operations. For example, to alloy Ti 6Al-4V with 43 weight percent tantalum, in the first melting operation the Ti-6Al-4V bar holes may be filled with 22 weight percent tantalum. After the first ingot is cast, holes are drilled again and filled with another 22 weight percent tantalum and the melting is repeated. Other sequences and magnitudes of Ta adds are made to reach the final alloy with 43 weight percent Ta. This approach is Ta elemental segregation in the ingot if it is added in smaller amounts in multiple melting and ingot casting steps. In addition, homogenization heat treatments between melts can reduce the amount of elemental diffusion needed. Other difficult to melt alloys can be produced by this method such as Ta—Nb, Nb—Zr, Ti—Nb, and Fe—Pt alloy systems. In other embodiments, the additive can be provided in the form of powder or chips rather than a solid wire or rod. The alloying that occurs in the melting and ingot casting process can be further improved by performing a homogenization (elemental diffusion) heat treatment to the ingots between melting operations. Mechanical alloying melting, casting, and heat treating operations can be performed at commercial sources such as Pittsburgh Materials Technology Inc. (Pittsburgh, Pa.), Applegate Group (Woodcliff Lake, N.J.) or Albany Research Center (Albany, Oreg.).

The alloy tubing is formed into stent. For example, selected portions can be removed to define bands and struts. The portions can be removed by laser cutting, as described, for example, in U.S. Pat. No. 5,780,807. In certain embodiments, during laser cutting, a liquid carrier, such as a solvent, gas, or an oil, is flowed through the tube. The carrier can prevent drops formed on one portion from re-depositing on another portion, and/or reduce formation of recast material on the tubular member. Other methods of removing portions of tubular member include mechanical machining (e.g., micro-machining), electrical discharge machining (EDM), photoetching (e.g., acid photoetching), and/or chemical etching.

The stent can further be finished, e.g., electropolished to a smooth finish, according to conventional methods. In some embodiments, about 0.0001 inch of material can be removed from the interior and/or exterior surfaces by chemical milling and/or electropolishing. The stent can be annealed to refine the mechanical and physical properties of the stent.

In use, the stent can be used, e.g., delivered and expanded, using a catheter. Suitable catheter systems are described in, for example, Wang U.S. Pat. No. 5,195,969, and Hamlin U.S. Pat. No. 5,270,086. Suitable stents and stent delivery are also exemplified by the Express, Radius® or Symbio® systems, available from Boston Scientific Scimed, Maple Grove, Minn.

The stent can be of any desired shape and size (e.g., coronary stents, aortic stents, peripheral vascular stents, gastrointestinal stents, urology stents, and neurology stents). Depending on the application, the stent can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stent 100 can be balloon-expandable, self-expandable, or a combination of both (e.g., U.S. Pat. No. 5,366,504).

The stent can also be a part of a stent-graft. In other embodiments, the stent includes and/or be attached to a biocompatible, non-porous or semi-porous polymer matrix made of polytetrafluoroethylene (PTFE), expanded PTFE, polyethylene, urethane, or polypropylene. The endoprosthesis can include a releasable therapeutic agent, drug, or a pharmaceutically active compound, such as described in U.S. Pat. No. 5,674,242, U.S. Ser. No. 09/895,415, filed Jul. 2, 2001 and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics.

The methods and the embodiments described above can be used to form medical devices other than stents and stent-grafts. For example, the methods and/or materials can be used to form filters, such as removable thrombus filters described in Kim et al., U.S. Pat. No. 6,146,404; in intravascular filters such as those described in Daniel et al., U.S. Pat. No. 6,171,327; and in vena cava filters such as those described in Soon et al., U.S. Pat. No. 6,342,062. The methods and/or materials can be used to form guidewires, such as a Meier steerable guidewire. The methods and/or materials can be used to form vaso-occlusive devices, e.g., coils, used to treat intravascular aneurysms, as described, e.g., in Bashiri et al., U.S. Pat. No. 6,468,266, and Wallace et al., U.S. Pat. No. 6,280,457. The methods and/or materials can be used to form wire to make catheter reinforcement braid. The methods and/or materials can also be used in surgical instruments, such as forceps, needles, clamps, and scalpels.

Further embodiments are provided in the following examples.

EXAMPLES

Example 1

A titanium-tantalum alloy with a mass absorption coefficient of at least 1.96 cm²/g (iron) and as high as 2.86 cm²/g (half of tantalum) is formulated as follows. The atomic mass coefficient for titanium is 1.21 and for tantalum is 5.72.

The following equation is used to provide desired radiopacity.

[Atomic % Ti×1.21]+[atomic % Ta×5.72]=1.96 to 2.86 cm2/g.

solving far x:

(x)(1.21)+(1−x)(5.72)=1.96cm2/g or 2.86 cm2/g x=0.83 (83 atomic percent Ti) or 0.63 (63 atomic percent TI)

or conversely 17 atomic percent Ta or 37 atomic percent Ta.

Conversion of atomic percent to weight percent for the 17 Ta-83 Ti alloy is as follows:

In $10^{23}$ atoms of Ti—Ta alloy, there are $0.17\times10^{23}$ atoms of Ta and $0.83\times10^{23}$ atoms of Ti.

$0.17\times10^{23}$ atoms of Ta/$6.02\times10^{23}$ atoms/mole=0.028 moles of Ta $0.83\times10^{23}$ atoms of Ti/$6.02\times10^{23}$ atoms/mole=0.138 moles of Ti (0.028 moles Ta)(180.95 grams/mole atomic weight)= 5.07 grams of Ta (0.138 moles Ti)(47.88 grams/mole atomic weight)= 6.61 grams of Ti 5.07 grams Ta+6.61 grams Ti=11.68 grams of alloy 6.61g Ti/11.68g=57 weight percent Ti in alloy.

5.07g Ta/11.68g=43 weight percent Ta in alloy.

An alloy of 83 atomic percent Ti and 17 atomic percent Ta (57 weight percent Ti and 43 weight percent Ta) has a calculated mass absorption coefficient equivalent to iron and a radiopacity similar to 316L stainless steel. An alloy of 63 atomic percent Ti and 37 atomic percent Ta (31 weight percent Ti and 69 weight percent Ta) has a calculated mass absorption coefficient equivalent to one-half of tantalum. The alloy constituents have magnetic susceptibility less than $3.5\times10^{-3}$ and are soluble in each other. The tantalum-titanium binary phase diagram (ASM Handbook, Volume 3 Alloy Phase Diagrams, ASM International, 1992, p. 2.374) indicates a 43 to 69 weight percent tantalum to be soluble in titanium as a solid solution two-phase (alpha and beta) material at room temperature. The tantalum-titanium binary phase diagram also indicates that the alloys with 43 to 69 percent tantalum concentration have alpha and beta phase microstructures. No brittle phases are evident in the phase diagram.

Example 2

A titanium-molybdenum alloy with a mass absorption coefficient of at least 1.96 cm²/g (iron) and as high as 2.86 cm²/g (half of tantalum) is formulated as follows.

The following equation is used to determine desired radiopacity.

[Atomic % Ti×1.21]+[atomic % Mo×7.04]=1.96 to 2.86 cm2/g.

(x)(1.21)+(1−x)(7.04)=1.96cm2/g or 2.86 cm2/g x=0.87 (87 atomic percent Ti) or 0.72 (72 atomic percent Ti) or conversely 13 atomic percent Mo or 28 atomic percent Mo.

Conversion of atomic percent to weight percent for the 13 Mo-87 Ti alloy:

In $10^{23}$ atoms of Ti—Mo alloy, there are $0.13\times10^{23}$ atoms of Mo and $0.87\times10^{23}$ atoms of Ti.

$0.13\times10^{23}$ atoms of Mo/$6.02\times10^{23}$ atoms/mole=0.022 moles of Mo $0.87\times10^{23}$ atoms of Ti/$6.02\times10^{23}$ atoms/mole=0.145 moles of Ti (0.022 moles Mo)(95.94 grams/mole atomic weight) =2.11 grams of Mo (0.145 moles Ti)47.88 grams/mole atomic weight) =6.94 grams of Ti 2.11 grams Mo+6.94 grams Ti=9.05 grams of alloy 6.94g Ti/9.05g=77 weight percent Ti in alloy.

2.11g Mo/9.05g=23 weight percent Mo in alloy.

An alloy of 87 atomic percent Ti and 13 atomic percent mo (77 weight percent Ti and 23 weight percent Mo) has a calculated mass absorption coefficient equivalent to iron and a radiopacity similar to 316L stainless steel. An alloy of 72 atomic percent Ti and 28 atomic percent Mo (56 weight percent Ti and 44 weight percent Mo) has a calculated mss absorption coefficient equivalent to one-half of tantalum and therefore has half the radiopacity of tantalum. The alloy constituents have magnetic susceptibility less than $3.5\times10^{-3}$ and that are soluble in each other. The molybdenum titanium binary phase diagram indicates (ASM Handbook, Volume 3 Alloy Phase Diagrams, ASM International, 1992, p. 2.296) 23 to 44 weight percent molybdenum to be soluble in titanium as a solid solution single (beta) or two-phase (alpha and beta) material at room temperature. The molybdenum-titanium binary phase diagram also indicates that alloys with 23 to 44 percent molybdenum concentration will have beta or beta plus alpha phase microstructures which are common in commercialized titanium engineering alloys such as Ti-6Al-4V. Cooling through the temperature range of about 850 to 695° C. can be performed rapidly (e.g., by argon gas, air cool, or liquid quenchant) to avoid precipitation of significant amounts of alpha-prime, alpha-double prime, or omega phases.

Example 3

A method for making an alloy of Ti-6Al-4V ELI with 43 weight percent Ta follows.

Procure a 3" diameter round bar of Ti-6Al-4V ELI (such as form Titanium Industries, Inc. in Morristown, N.J.) and cut to 5.5 inches long. Procure 0.5" diameter tantalum rod (such as from Rembar, Dobbs Ferry, N.Y.) and cut into lengths of 3.25". Drill eight holes into the titanium bar that are 0.55/0.6" diameter and 4.5" deep. Put the eight 3.25" long pieces of 0.5" diameter tantalum rod into the holes. Heat the assembly in a vacuum furnace at 1400° C. for 8 hours and vacuum cool. Gas tungsten arc weld (GTAW or TIG) the assembly with the hole-end up to the vacuum arc remelt (VAR) electrode holder. Vacuum arc remelt the assembly and cast an ingot. Heat the ingot in a vacuum furnace at 1400° C. for 8 hours and vacuum cool. Repeat the VAR and heat treatment once ore or multiple times. Machine the ingot into a 2.5" diameter×4" long billet. Convert billet to annealed seamless tent tubing.

Example 4

Arc melted Ti—Ta alloy button ingots were prepared. Two ingots were melted from a 50-50 mixture (by weight) of Ti-6Al-4V and tantalum rods. One ingot was melted from a 50-50 mixture (by weight) of pure titanium and tantalum rods. Cold rolling and annealing of the ingots were used to form strips for mechanical and physical property testing.

The ingots were prepared from the following rods and charge materials procured from Goodfellow Corporation, Berwyn, Pa.

TABLE V

Rods

| Material | Traceability |
|---|---|
| Ti—6Al—4V rods | Goodfellow LS251817JV; TI017910/1, 5 mm dia × 200 mm long rods, 10 pcs, 174 g, annealed |
| Ta rods | Goodfellow LS251817JV, TA007920/8, 99.9% pure, 2 mm dia × 200 mm long rods, 5 pcs, 53.2 g, annealed |
| Ti rods | Goodfellow LS251817JV, TI007910/12, 2 mm dia × 100 mm long rods, 20 pcs, 28.5 g, 99.6% pure, annealed |

TABLE VI

Arc Melter Charge Materials

| Ingot # | Ti—6Al—4V, grams | Ti, g | Ta, g | # of melt cycles | Ingot mass, g |
|---|---|---|---|---|---|
| 2 & 3 | 26.0 | | 25.8 | 3 | 51.7 |
| 1 | | 27.6 | 26.5 | 3 | 53.9 |

The rods were cut into lengths of 1-2", cleaned in acetone, and weighed on a digital scale. The rods were divided up by weight into two groups for melting. The raw materials were melted in an arc melter (Model MRF ABJ-900, Materials Research Furnaces, Inc., Suncook, N.H.). The arc melter was operated at 350-400 amps. Three melt cycles were performed for each alloy.

Figure 5:
FIGS. 5-8 are photo micrographs.

Referring to FIG. 5, a photomacrograph shows the three ingots after arc melting. The ingot on the left is the Ti-50Ta alloy. The other two ingots are the 50 (Ti-6Al-4V)-50Ta alloy. After melting, each ingot was struck ten times with a hammer to see if it would crack or fracture. All three of the ingots withstood the hammer test without cracking or fracturing and the ingot deformed when hit. This test was performed as an assessment of the formability of the material. Cracking can indicate that the alloy is too brittle for cold rolling.

Three 0.20-0.25" thick bars were used as a starting stock for cold rolling. The machined dimensions of the rolling blanks are listed in the following table.

TABLE VII

Dimensions of Rolling Blanks

| Bar # | Length, inches | Width, inches | Thickness, inches |
|---|---|---|---|
| 1 (Ti—Ta) | 3.06 | 0.57 | 0.23 |
| 2 (Ti64—Ta) | 2.17 | 0.57 | 0.23 |
| 3 (Ti64—Ta) | 1.12. | 0.49 | 0.24 |

The machined bars were cold rolled to a total reduction in thickness of 50%. The dimensions after cold rolling are listed in the following table.

TABLE VIII

Dimensions after 1st Cold Rolling

| Bar # | Length, inches | Thickness, inches |
|---|---|---|
| 1 (Ti—Ta) | 4.7 | 0.10 |
| 2 (Ti64—Ta) | 3.2 | 0.10 |
| 3 (Ti64—Ta) | 1.7 | 0.10 |

Figure 6:
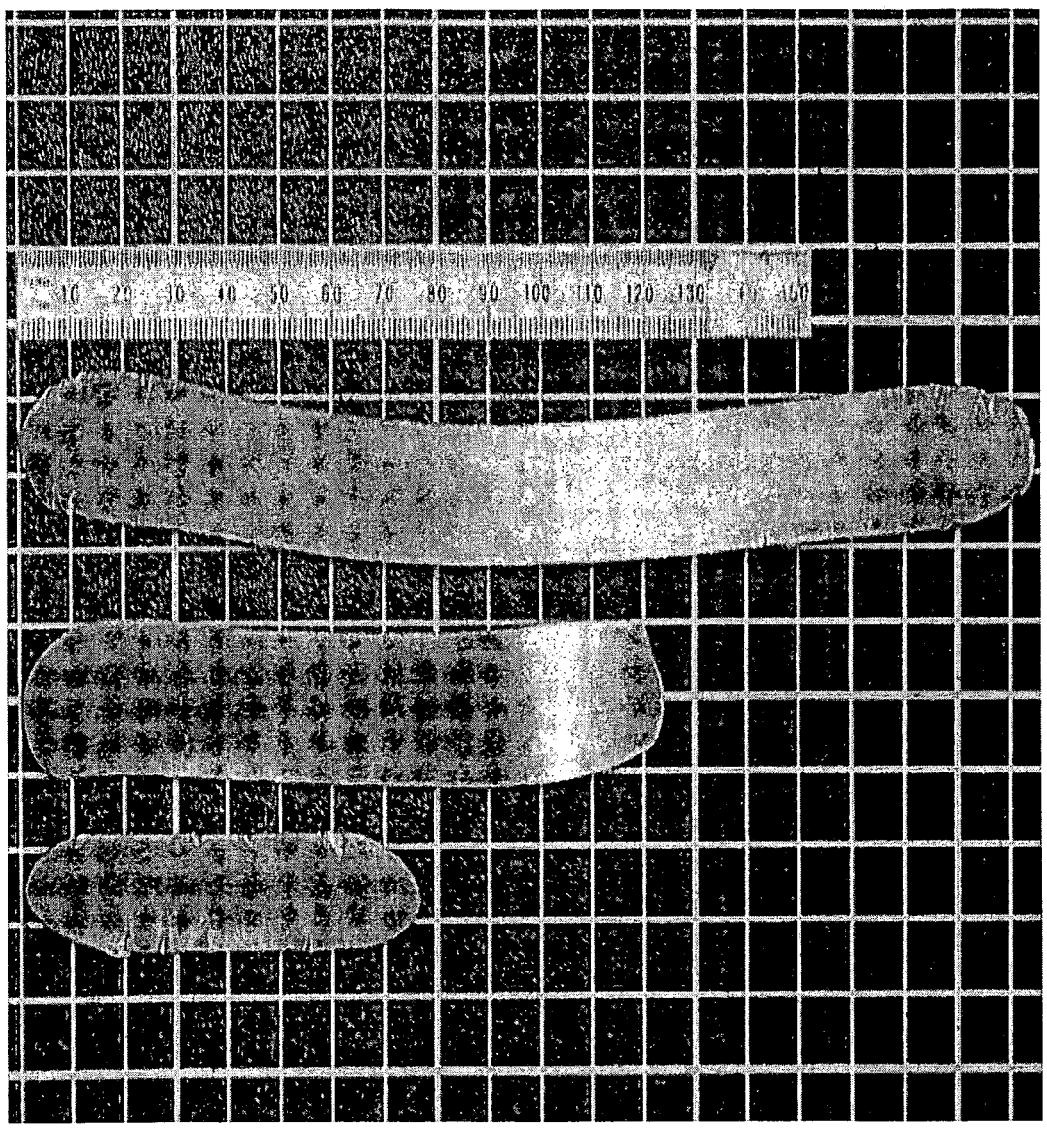

The cold rolled strips were annealed in the a vacuum heat treat furnace at 1200° C. for 60 minutes in vacuum followed by a vacuum cool. The purpose of this heat treatment was to continue to homogenize the alloy, recrystallize the cold worked microstructure, and soften the material to allow for further cold rolling. Referring to FIG. 6, fine fissures were observed on the surface of the strips. Strip #3 had small edge cracks along the length. None of these flaws were judged to be severe enough to impair further cold rolling.

The three strips were cold rolled to a total reduction in thickness of −50%. The dimensions of the rolled strips are listed in Table IX.

TABLE IX

Dimension of Strips After Second Cold Rolling

| Bar # | Length, inches | Width, inches | Thickness, inches |
|---|---|---|---|
| 1 (Ti—Ta) | 7.75 | 0.75 | 0.058 |
| 2 (Ti64—Ta) | 4.87 | 0.81 | 0.058 |
| 3 (Ti64—Ta) | 3.00 | 0.62 | 0.058 |

Figure 7:
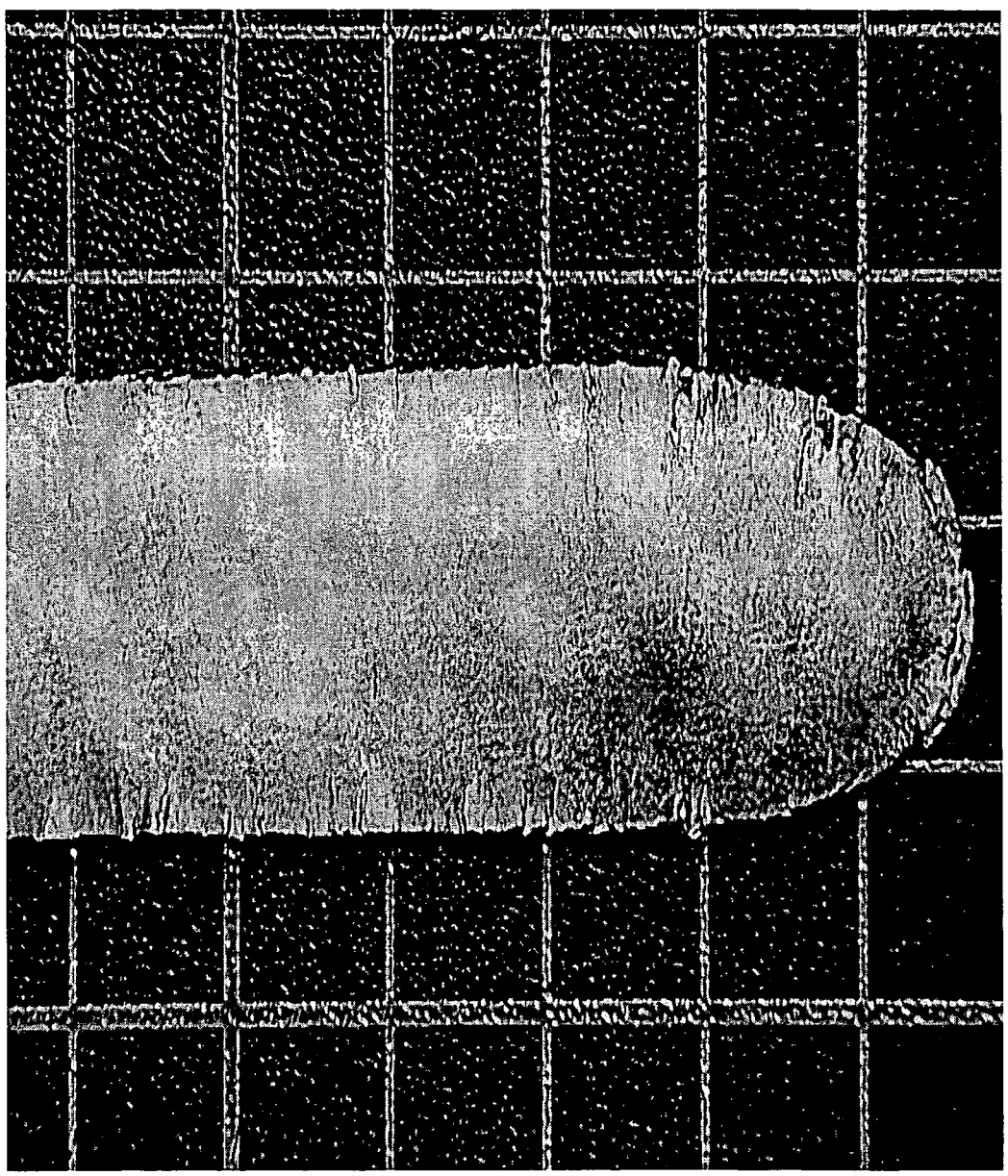

Referring to FIG. 7, the surface and edges of the strips were examined without magnification. Strip #1 had fine edge cracks. Strip #2 had no cracks. Strip #3 had edge cracks.

The cold rolled strips were annealed in the vacuum heat treat furnace at 1000° C. for 30 minutes in vacuum followed by a vacuum cool. The purpose of this heat treatment was to recrystallize the cold worked microstructure and soften the material to allow further cold rolling. The strips were cold rolled to 0.025" thickness. The dimensions are given in Table X.

TABLE X

Dimension of Strips After Third Cold Rolling Campaign

| Bar # | Length, inches | Width, inches | Thickness, inches |
|---|---|---|---|
| 1 (Ti—Ta) | 9 and 8 | 079 | 0.025 |
| 2 (Ti64—Ta) | 10 | 0.88 | 0.025 |
| 3 (Ti64—Ta) | 6 | 0.65 | 0.025 |

Figure 8:
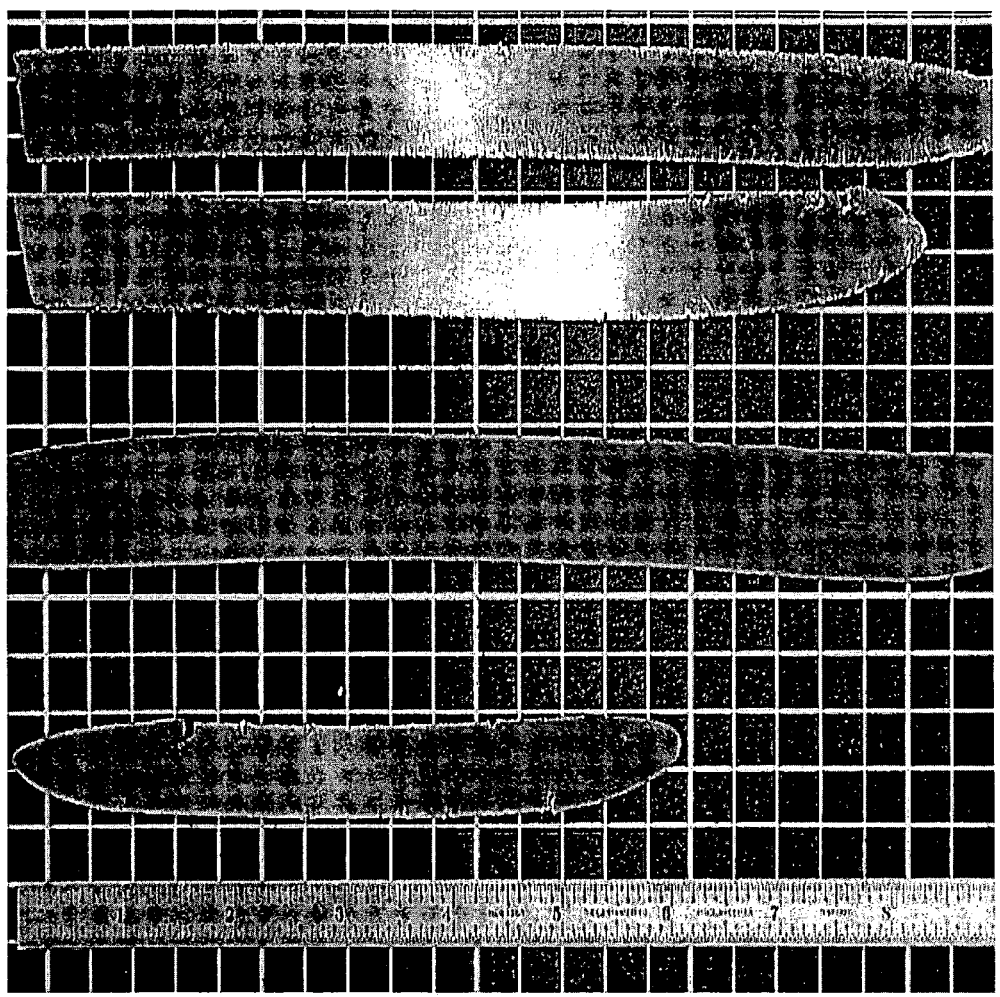

Referring to FIG. 8, Strips #1 and #3 had many small edge cracks. Strip #2 did not have edge cracks.

The strips were beta solution treated in a vacuum heat treat furnace at 850° C. for 30 minutes and cooled in vacuum. The strips were submitted for metallography. The strips were subjected to tensile specimen machining and testing (Metcut Research Associates, Inc. (Cincinnati, Ohio)). The tensile results were 85-115 ksi UTS, 65-105 YS, and 5-25% elongation.

Ti-6Al-4V, pure titanium, and tantalum materials had been melted in powder metal form. Sometimes the ingots did not have sufficient formability to allow cold rolling to a final reduction in thickness of 50%. The large surface area of fine powder metal may allow for significant contamination to be carried into the ingot thereby reducing the ductility of the alloy. In this experiment, solid rods were used instead of powder metal for the furnace charges. The smaller surface area of the rods (relative to the powder) should result in better ingot ductility.

All publications, applications, references, patents referred to in this application are herein incorporated by reference in their entirety.

Other embodiments are within the claims.

What is claimed is:

1. A balloon-expandable medical stent, comprising:
a generally tubular body including an alloy having Ti at about 50 weight percent, about 10 weight percent of Zr, and about 40 weight percent of Ta, the alloy having a yield strength of about 45 ksi or more, a magnetic susceptibility of about +1 or less, and a mass absorption coefficient of about 1.9 cm$^2$/g or more.

2. The stent of claim 1 wherein the alloy has a UTS of about 90 ksi or more and the percent tensile elongation is about 40 or more.

3. The stent of claim 1 wherein the yield strength is about 50 ksi or greater, the percent strength to peak load is about 30 or greater, the UTS is about 90 ksi or greater, and the percent strength to fracture is about 40 or greater.

4. The stent of claim 1 wherein the magnetic susceptibility is about 3.5×10−3 or less.

5. The stent of claim 1 wherein the mass absorption coefficient is about 2.9 cm$^2$/g or less.

6. The stent of claim 1 wherein the tubular body includes wall portions having a thickness of about 0.0015 inch to about 0.0150 inch.

7. The stent of claim 1 wherein the tubular body includes a therapeutic agent.

8. A balloon-expandable medical stent, comprising:
a generally tubular body including an alloy comprising:
about 40 weight percent of Ta;
about 50 weight percent of Ti; and
about 10 weight percent of Zr.

* * * * *

UNITED STATES PATENT AND TRADEMARK OFFICE
CERTIFICATE OF CORRECTION

PATENT NO. : 8,137,614 B2
APPLICATION NO. : 12/643629
DATED : March 20, 2012
INVENTOR(S) : Jonathan S. Stinson Page 1 of 1

It is certified that error appears in the above-identified patent and that said Letters Patent is hereby corrected as shown below:

1.) Column 14, Claim 4, Line 6: delete "3.5×10-3" and insert --$3.5 \times 10^{-3}$--.

Signed and Sealed this
Fifth Day of June, 2012

David J. Kappos
*Director of the United States Patent and Trademark Office*